United States Patent [19]

Schneck

[11] Patent Number: 5,316,590
[45] Date of Patent: May 31, 1994

[54] METHOD FOR CLEANING AND LUBRICATING A DENTAL HANDPIECE WITH A DISPOSABLE CONTAINER

[75] Inventor: Gary G. Schneck, Algonquin, Ill.
[73] Assignee: Gendex Corporation, Des Plaines, Ill.
[21] Appl. No.: 20,659
[22] Filed: Feb. 22, 1993
[51] Int. Cl.$^5$ ............................................. B08B 3/00
[52] U.S. Cl. ........................................ 134/26; 134/42; 134/182; 206/368; 433/116
[58] Field of Search .............. 134/22.1, 26, 32, 42, 134/92, 93, 94.1, 95.1, 182; 433/116, 104; 206/368

[56] References Cited
U.S. PATENT DOCUMENTS

| | | | |
|---|---|---|---|
| 4,218,216 | 8/1980 | Sugai et al. | 433/104 |
| 4,446,967 | 5/1984 | Halkyard | 206/368 |
| 4,552,163 | 11/1985 | Biancalana et al. | 134/56 R X |
| 4,990,087 | 2/1991 | De Rocchis et al. | 433/104 |
| 5,165,503 | 11/1992 | Hoffman | 433/104 |

Primary Examiner—R. Bruce Breneman
Assistant Examiner—Saeed T. Chaudhry
Attorney, Agent, or Firm—Trexler, Bushnell, Giangiorgi & Blackstone, Ltd.

[57] ABSTRACT

A novel disposable container and method is used for cleaning and lubricating a standard dental handpiece. The disposable container completely encloses a head of the dental handpiece. When the handpiece is cleaned or lubricated with cleaning or lubricating agents, the container collects cleaning or lubricating agents and any other materials that are expelled therewith from the handpiece to prevent these materials from entering the atmosphere.

3 Claims, 1 Drawing Sheet

METHOD FOR CLEANING AND LUBRICATING A DENTAL HANDPIECE WITH A DISPOSABLE CONTAINER

BACKGROUND OF THE INVENTION

The present invention generally relates to method for cleaning and lubricating a dental handpiece and to an apparatus which may be employed in this method. More specifically, the invention relates to a disposable container that prevents materials that are expelled from the handpiece during cleaning or lubrication from entering the atmosphere.

Current standards of dental practice require sterilization of dental handpieces between patients. However, the handpiece must be cleaned before going into the sterilizer. This usually includes cleaning the turbine and internal parts. In normal procedures, a cleaning fluid is circulated throughout the dental handpiece by connecting the handpiece to a suitable supply of cleaning fluid and energizing the handpiece. The cleaning fluid and any residue which are expelled through the head of the handpiece escape into the atmosphere. Additionally, after the sterilization of the handpiece has been completed, the handpiece will usually require lubrication. Again, the handpiece is connected to a suitable supply of lubricating fluid and energized. Any excess lubricating fluid which is expelled through the head escapes into the atmosphere.

Dental professionals have started using elaborate devices that flush, disinfect and lubricate the handpiece. However, this merely creates another device which must be cleaned and disinfected or sterilized. Furthermore, such devices are often expensive.

The present invention presents a novel apparatus and method intended to minimize these problems, as well as to present several other improvements.

OBJECTS AND SUMMARY OF THE INVENTION

A general object of the present invention is to provide an apparatus and method for cleaning and lubrication a dental handpiece.

Another object of the present invention is to provide an apparatus and method for capturing materials expelled from the head of a dental handpiece during cleaning or lubrication.

Briefly, and in accordance with the foregoing, the present invention comprises a novel apparatus and method for cleaning and lubricating a standard dental handpiece. The apparatus comprises a disposable container which completely encloses a head of the dental handpiece. When the handpiece is cleaned or lubricated with cleaning or lubricating agents, the container collects the cleaning or lubricating agents and any other materials which are expelled therewith from the handpiece and prevents the expelled materials from entering the atmosphere.

BRIEF DESCRIPTION OF THE DRAWINGS

The features of the invention which are believed to be novel are set forth with particularity in the claims. The organization and manner of operation of the invention, together with further objects and advantages thereof, may best be understood by reference to the following description, taken in connection with the accompanying drawings, wherein like reference numerals identify like elements and in which:

DETAILED DESCRIPTION OF THE ILLUSTRATED EMBODIMENT

Figure 1:
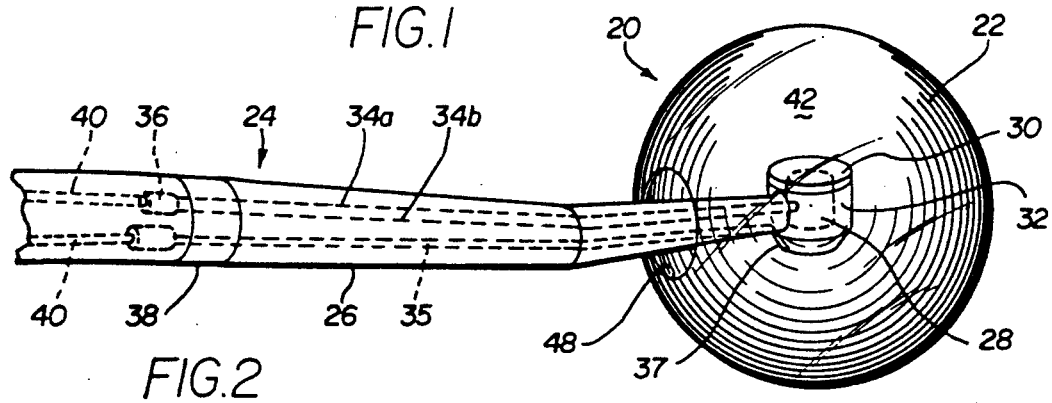
FIG. 1 is a perspective view of a dental handpiece and apparatus according to a first embodiment of the present invention.

While the invention may be susceptible to embodiment in different forms, there is shown in the drawings, and herein will be described in detail, specific embodiments with the understanding that the present description is to be considered an exemplification of the principles of the invention, and is not intended to limit the invention to that as illustrated and described herein.

Referring initially to FIG. 1, the apparatus of the invention may be embodied in a container 20 which is used to capture materials 22 that are expelled from the head of a dental handpiece 24 during cleaning or lubrication. This prevents such materials from entering the atmosphere or at least minimizes the amount of such materials. The container 20 is used with a standard dental handpiece 24 that generally includes a handle 26, a head 28 with an opening 30, a turbine 32 housed in the opening 30 of the the head 28 and fluid conduit means 34a and 34b which include connective fittings 36 extending from a rear portion 38 of the handpiece 24 for passing fluid from a supply means 40 through the handpiece 24 to the head 28 and turbine 32. In normal use, a fluid such as compressed air is delivered through the conduit 34a to energize the turbine 32, i.e., cause the turbine 32 to rotate. Conduit 34b acts as an air exhaust conduit. Other conduits, such as a water conduit 35 may also be provided. Water conduit 35 has an exit 37 adjacent the head 30.

The container 20 may take any of several forms. In the preferred embodiment and as shown in the drawings, the container 20 takes on a generally spherical shape. However, it is to be understood that the container 20 could take on another shape without departing from the invention. The container 20 is sized to completely enclose the head 28 of the dental handpiece 24 while leaving enough space to receive fluids and other materials 22 expelled from the head 28 during cleaning or lubrication.

The container 20 may be made of a suitable plastic material and the like. Advantageously, the container 20 is designed to be simple and inexpensive and readily disposable after a single use.

Figure 2:
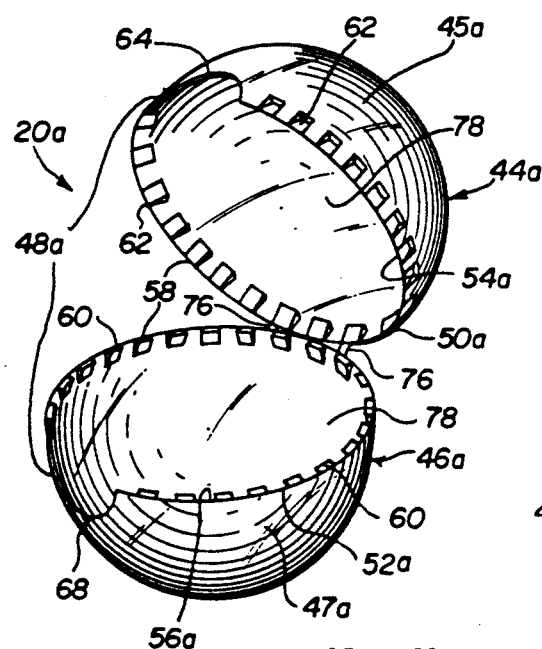
FIG. 2 is a perspective view of an apparatus according to a second embodiment of the present invention.
Figure 3:
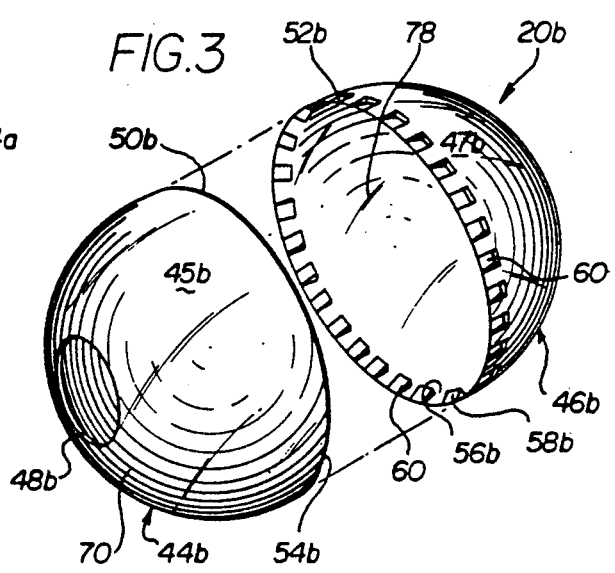
FIG. 3 is a perspective view of an apparatus according to a third embodiment of the present invention.
Figure 4:
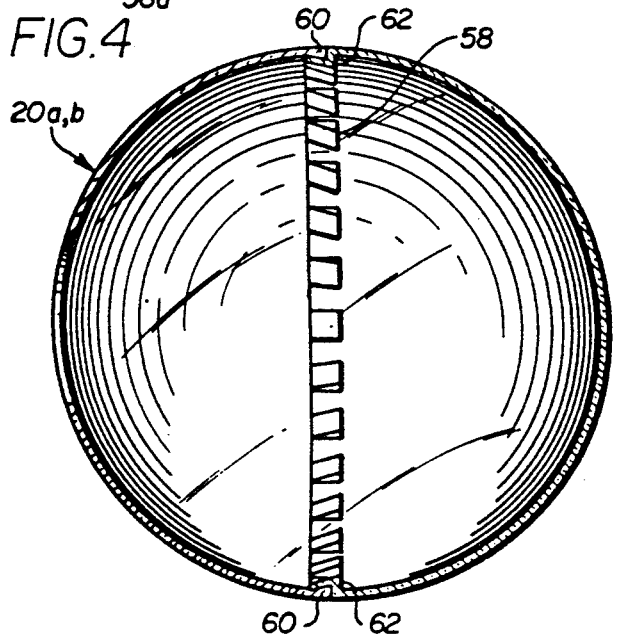
FIG. 4 is a cross sectional view showing the embodiments of FIG. 2 or 3 in an assembled condition.

As shown in FIG. 1, the container 20 may be provided as a single piece defined by an exterior wall 42. As shown in FIGS. 2 and 3, the container 20a, 20b may be made of two separate hollow hemispheres 44a, 44b and 46a, 46b defined by walls 45a, 45b and 47a, 47b that can be snapped together or otherwise inter-engaged to form a complete sphere. The embodiments of FIGS. 2 and 3 may be preferable in that they will allow for easier bulk packaging and storage, since the hemispheres can be nested or stacked.

Each of the embodiments of FIGS. 1–3 has a through opening or aperture 48, 48a, 48b thereon which is sized for receiving the head 28 of a dental handpiece 24 therethrough. The head 28 of the handpiece 24, when inserted into the container 20, will be completely enclosed. A portion of the handle 26 will be inserted into the container 20, however, a portion of the handle 26 will also extend outwardly of the container 20 through the opening 48. The container 20 encloses the head 28 in such a manner such that the container 20 only contacts the handpiece 24 along the handle 26.

In FIGS. 2 and 3, the container 20 is formed from two generally equal hemispheres 44a, 44b and 46a, 46b. Each hemisphere 44a, 44b and 46a, 46b terminates in a rim 50a, 50b and 52a, 52b having a circular periphery. The hemispheres are snapped together to form a complete sphere. In order to do this, lips 54a, 54b and 56a, 56b along the rims 50a, 50b and 52a, 52b are placed in an overlapping relation and secured by interlocking means 58.

The interlocking means 58 may take one of many forms. In the illustrated embodiment, one lip 54a, 54b has a series of spaced protruding nibs 60 along the interior of the circular periphery of the rim 50a, 50b. The other lip 56a, 56b has a series of spaced recessed portions 62 that are complementary to the protruding nibs 60 along the exterior of the circular periphery of the rim 52a, 52b. In order to snap the two hemispheres 44a, 44b and 46a, 46b together, the two lips 54a, 54b and 56a, 56b are placed in an overlapping relationship and the series of recessed portions 62 accepts the series of protruding nibs 60 therein.

In FIG. 2, respective halves 64 and 68 of the aperture 48a are located on each hemisphere 44a and 46a along each rim 50a and 52a. When the two hemispheres 44a and 46a are snapped together, the halves 64 and 68 of the aperture 48a must be aligned to allow the dental handpiece 24 to enter into the container 20a. In FIG. 3, the aperture 48b is located at the bottom portion 70 of a single hemisphere 44b approximately centered relative to the circular rim 50b of the hemisphere 44b. The aperture 48a, 48b may be located in other positions relative to hemispheres 44b, 46b or otherwise divided between the the two hemispheres 44a, 46a without departing from the invention.

Figure 5:
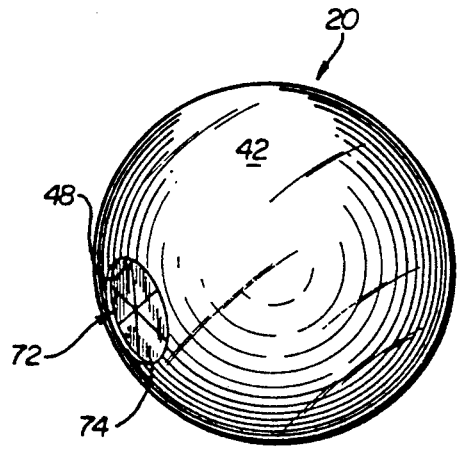
FIG. 5 is a simplified perspective view of the apparatus of the present invention showing a modified form of an opening.

Referring to FIG. 5, the apertures 48, 48a, 48b may include sealing means such as a flexible membrane 72 extending inwardly from an inner periphery of aperture 48, 48a, 48b. The membrane 72 may take on any of several forms. In the preferred embodiment, the membrane 72 comprises a plurality of flexible fingers 74 in a triangular shape. The membrane 72 will tend to form at least a partial seal around the handle 26 of the handpiece 24. When the head 28 is inserted, the membrane 72 will flex around the shape of the head 28 and allow it to pass through. Once the head 28 passes through, the membrane 72 will generally conform to the shape of the handle 26. Thus, the aperture 48, 48a, 48b will be in even closer engagement with handpiece 24 such that the material 22 that is expelled from the handpiece 24 will tend not to escape the container.

Another feature that may be included in the design of the disposable container is a hinge or hinges 76 as shown in FIG. 2, which, may also be used in the embodiment of FIG. 3. The hinge or hinges 76 may be made of a resilient material or pliable plastic or may be molded or otherwise formed as an integral part of hemispheres 44a, 46a and connects the two hemispheres 44a and 46a. The hinge or hinges 76 facilitate the aligning of the halves 64, 68 of the aperture 48a, in the embodiment of FIG. 2, and also of the hemispheres 44a and 46a generally for engagement of the lips 54, 56 and interlocking means 58. The hinge 76 will also prevent a single hemisphere 44a or 46a from being misplaced and retain hemispheres in properly matched pairs.

Having disclosed the construction of the container 20, a method of cleaning and lubricating a dental handpiece will now be discussed. When using the embodiments of FIGS. 2 or 3, the container 20a, 20b is first assembled. The lips 54a, 54b and 56a, 56b are placed in an overlapping relationship and locked into place as described hereinabove.

Next, the head 28 of the dental handpiece 24 and part of the handle 26 are inserted into the container. In doing so, the membrane 72 (if one is provided) flexes as the head 28 passes through and then conforms generally to the shape of the handle 26.

The dental handpiece 24 is attached by the fittings 36 to a cleaning fluid supply means 40. The handpiece 24 is then energized. The fluid containing cleaning agents is drawn out of the supply means 40 through the conduit 34 to the head 28 and turbine 32. When the fluid enters the head 28 and turbine 32, excess cleaning fluid and other materials 22 that have amassed on the dental handpiece 24 will be expelled through the head 28 and from the turbine 32. The container catches all of the excess cleaning fluid and materials 22 along its inner surface 78. Thus, the excess cleaning fluid and materials 22 are not expelled into the atmosphere. Cleaning fluid may also be fed through water conduit 35 and expelled at its outlet 37 to be captured in the container.

When the handpiece 24 has been cleaned, the handpiece 24 is de-energized and removed from the container. The container is then thrown away. Thereafter, the dental handpiece 24 is sterilized.

After sterilization, the handpiece 24 may be lubricated. In order to prevent excess lubricant from being expelled into the atmosphere, a second container is used in the same fashion as described above with reference to the cleaning process.

The dental handpiece 24 is then attached by the fittings 36 to a lubricant supply means. The handpiece 24 is energized. Lubricant is drawn through the conduit 34 to the head 28 and turbine 32. When the lubricant enters the head 28 and turbine 32, excess lubricant will be expelled through the head 28 and from the turbine 32. The second container catches the excess lubricant along its inner surface 78. Thus, the excess lubricant is not expelled into the atmosphere.

When the handpiece 24 is lubricated, the handpiece 24 is de-energized and removed from the container. The container is then thrown away. The dental handpiece 24 is now ready for use.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiments and specific construction described herein but should be defined by the appended claims and equivalents thereof. Accordingly, the aim in the appended claims is to cover all such changes and modifications as fall within the true spirit and scope of the invention.

The invention is claimed as follows:

1. A method of cleaning and lubricating a dental handpiece that includes a handle, a head for mounting a turbine, and channels for allowing fluids to travel from the handle to the head, said method comprising the steps of:
   (a) providing a disposable container having an opening sized to receive the head of the dental handpiece therethrough;
   (b) inserting the head of the dental handpiece through the opening in the disposable container with at least a portion of the handle projecting outwardly of the disposable container;
   (c) passing one of a cleaning fluid and a lubricating fluid through said channels from said handle to said head until said fluid is expelled from said head, and
   (d) collecting the expelled fluid and any materials carried therewith along an inner surface of the disposable container, said opening being sized such that said expelled fluid and any materials carried therewith are substantially retained in said disposable container.

2. The method as defined in claim 1 further including the steps of:
   (d) disposing of the disposable container after the fluid has been collected; and
   (e) sterilizing the dental handpiece.

3. A method of cleaning and lubricating a dental handpiece that includes a handle, a head for mounting a turbine, and channels for allowing fluids to travel from the handle to the head, said method comprising the steps of:

providing a first disposable container having an opening sized to receive the head of the dental handpiece therethrough;

inserting the head of the dental handpiece through the opening in the first disposable container with at least a portion of the handle projecting outwardly of the disposable container;

passing a fluid containing cleaning agents through said channels from said handle to said head until said fluid is expelled from said head thereby cleaning the dental handpiece;

collecting the expelled fluid and any materials carried therewith along an inner surface of the first disposable container, said opening being sized such that said expelled fluid and any materials carried therewith are substantially retained in said first disposable container;

disposing of said first disposable container;

providing a second disposable container having an opening sized to receive the head of the dental handpiece therethrough;

inserting the head of the dental handpiece through the opening in the second disposable container with at least a portion of the handle projecting outwardly of the disposable container;

passing a fluid containing lubricating agents through said channels from said handle to said head until said fluid is expelled from said head thereby lubricating the dental handpiece;

collecting the expelled fluid and any materials carried therewith along an inner surface of the second disposable container, said opening being sized such that said expelled fluid and any materials carried therewith are substantially retained in said second disposable container; and disposing of said second disposable container.

* * * * *